(12) United States Patent
Hongerholt

(10) Patent No.: US 6,568,270 B2
(45) Date of Patent: May 27, 2003

(54) ULTRASONIC SENSOR SELF TEST FOR INTEGRITY/PERFORMANCE VERIFICATION

(75) Inventor: Derrick D. Hongerholt, Eagan, MN (US)

(73) Assignee: Rosemount Aerospace Inc., Burnsville, MN (US)

( * ) Notice: Subject to any disclaimer, the term of this patent is extended or adjusted under 35 U.S.C. 154(b) by 0 days.

(21) Appl. No.: 09/804,933

(22) Filed: Mar. 13, 2001

(65) Prior Publication Data

US 2002/0129654 A1 Sep. 19, 2002

(51) Int. Cl.[7] .............................................. G01N 29/24
(52) U.S. Cl. ....................................... 73/596; 73/170.26
(58) Field of Search ............................. 73/597, 598, 599, 73/600, 629, 627, 623, 170.21, 170.26, 1.82, 865.9; 340/580, 582

(56) References Cited

U.S. PATENT DOCUMENTS

| 4,037,465 A | | 7/1977 | Cook et al. ................. 73/67.8 |
|---|---|---|---|
| 4,254,660 A | * | 3/1981 | Prause ........................ 73/622 |
| 4,412,315 A | | 10/1983 | Flournoy ..................... 367/99 |
| 4,461,178 A | | 7/1984 | Chamuel ..................... 73/599 |
| 4,466,286 A | * | 8/1984 | Berbee et al. ................ 73/629 |
| 4,502,330 A | * | 3/1985 | Hawsen ....................... 73/623 |
| 4,833,660 A | | 5/1989 | Deom et al. ................. 367/157 |
| 5,095,754 A | | 3/1992 | Hsu et al. ..................... 73/602 |
| 5,357,228 A | | 10/1994 | Dufilie ........................ 333/195 |
| 5,456,114 A | | 10/1995 | Liu et al. ..................... 73/597 |
| 5,629,485 A | | 5/1997 | Rose et al. ................... 73/599 |
| 5,729,508 A | | 3/1998 | Baker et al. ................ 367/176 |
| 5,922,958 A | | 7/1999 | Schugt ........................ 73/596 |
| 6,378,377 B2 | * | 4/2002 | Matuseki et al. ............ 73/627 |

FOREIGN PATENT DOCUMENTS

EP          0 321 146 A2       6/1989

* cited by examiner

Primary Examiner—Helen Kwok
(74) Attorney, Agent, or Firm—Westman, Champlin & Kelly, P.A.

(57) ABSTRACT

A contaminant sensor is provided which has an ultrasonic guided wave transducer that is bonded to a wall in which the ultrasonic energy is transmitted. A detector reflector is provided at a selected distance from the transducer, which will reflect signals that are affected or changed by contaminants collecting on an exposed surface of the wall. A self test reflector is positioned closely adjacent to the transducer and provides a reflected signal that is substantially unaffected by contaminants on the exposed surface of the wall, but which reflects signals only when the transducer assembly is functioning properly, and is properly bonded to the wall. The signal that is reflected by the self test reflector changes when the bond loosens. The receiver is activated right after transmission ceases to determine if the transmitter is operating.

27 Claims, 2 Drawing Sheets

ULTRASONIC SENSOR SELF TEST FOR INTEGRITY/PERFORMANCE VERIFICATION

BACKGROUND OF THE INVENTION

The present invention relates to a self test system for use with an ultrasonic transducer mounted on a wave guide plate assembly or wall and which is used for contaminant detection. The ultrasonic transducer is bonded to the wave guide wall or plate, or other wave guide, and the self test procedure determines that the transducer is working and whether the transducer is aconstically bonded or coupled to the wall or pale.

In the prior art, acoustic channels or wave guides that have ultrasonic transducers bonded to one location, that transmit signals that are reflected from a reflector positioned at a spaced location have been known. The wave guide generally comprises a plate or sheet that has a surface exposed to ambient conditions. Snow, ice, or other contaminants that adhere to the exposed surface will cause changes (attenuation) in the reflected wave that is sensed by the transducer. The changes in the reflected wave indicate the presence of ice, as well as other contaminants.

U.S. Pat. No. 5,922,958 to Schugt shows such a detector device. The weakening or loosening of the bond between the transducer or transmitter and the plate can occur and some way of checking for adequate ultrasonic vibration coupling to the plate is. desired. When a sensor disbonds or in some way the bond fails the ultrasonic sensors will give spurious or no signals and a shortened sensor life. If there is heavy plate contamination, the guided wave signature or reflected signal received from the reflector near the end of the plate disappears, which can indicate that either the plate is truly contaminated, the transducer is not working, or a disbond occurred. The present invention provides a simple self test procedure that will provide information about the integrity and performance of ruse bond of the transducer, as well as its ability to function for determining contaminants on a surface of a wall or plate. Contaminant detected systems are also shown in Rose et al. U.S. Pat. Nos. 5,629,485 and 5,932,806.

SUMMARY OF THE INVENTION

The present invention relates to an ultrasonic vibration sensor, preferably formed as a wall or plate with a surface exposed to ambient elements, and which has an ultrasonic transducer, including a transmitter bonded to the wall or plate. The transmitter and a receiver for reflected or returned ultrasonic vibration can be combined and placed at one location, generally adjacent one end of a plate. An ultrasonic or acoustic vibration reflector is placed at a location spaced from the transmitter. Preferably, the reflector has a surface extending transversely to the direction of transmission of the ultrasonic energy at the opposite end of the sensor wall. The reflector, as shown may be a block bonded to the wall or plate.

A self test procedure is provided by placing a second known discontinuity, as shown a waveguide, in the plate or wall adjacent the ultrasonic vibration transmitter. The second discontinuity forms an ultrasonic wave reflector that will reflect any wave transmitted from the transducer. The preferred construction is a small waveguide bonded to the under surface of the wall or plate. Wave displacements normal to the plate surface would transfer into the waveguide, hit the end of the waveguide and reflect back toward the transducer. Other known reflectors close to the transmitter or transducer can be used. The second ultrasonic wave reflector that is positioned close to the transmitter is of less a disruption than the contaminate signal generating reflector near the end of the sensor wall. Because the test reflector is close to the transmitter, the signal received from the self test reflector is not attenuated by ice or other contaminants adhering to the opposite side of the wall or plate. The receiver circuit provides a signal indicating receipt of the signal reflected from the second discontinuity.

A processor circuit is connected to receive the signal related to the reflected wave from the second discontinuity. The process converts the signal that is received from the self test reflector into a readout indicating the transmitter is operating. If the transmitter has a failure or it has disbonded, there will be no signal.

Again, the self test reflector is close enough to the transmitter portion of the transducer so even with contaminants adhering to the exposed surface of the transmission wall or plate there will be a signal shape that will not change unless there is a disbond or other problem with the ultrasonic transducer itself. The length of the self test waveguide forming a reflector that is in contact with and bonded to the plate or wall is related to the wavelength of the ultrasonic energy in the plate to insure that the ultrasonic energy is transferred to the waveguide. Also, the overall length of the self test waveguide forming the self test reflector is selected to provide a time before having a return signal from the self test reflector so that any disturbances from internal reflection in the transducer or transducer mounting are abated. This insures that the internal reflections are not confused with or thought to be signals from the self test waveguide.

The self test reflector arrangement is easily formed or installed, and serves as a integrity check each time the transducer transmits an ultrasonic signal toward the contaminant detector.

It should be noted that while the preferred embodiment illustrates a bonded on waveguide for the self test and a bonded on block for the main contaminant detection, other types of reflectors can be utilized. For example, the surface on the plate opposite from the surface exposed to ambient conditions can have a groove or other known type formed in the plate. A rivet array in the wall can serve as the self test reflector as well. Further, the wall of a structure can transmit the ultrasonic signal, so a separate plate is not always necessary. The first reflector used for detecting contaminates can be replaced by a separate receiver positioned on wall or plate at the location disclosed for the reflector.

DETAILED DESCRIPTION OF THE PREFERRED EMBODIMENTS

Figure 1:
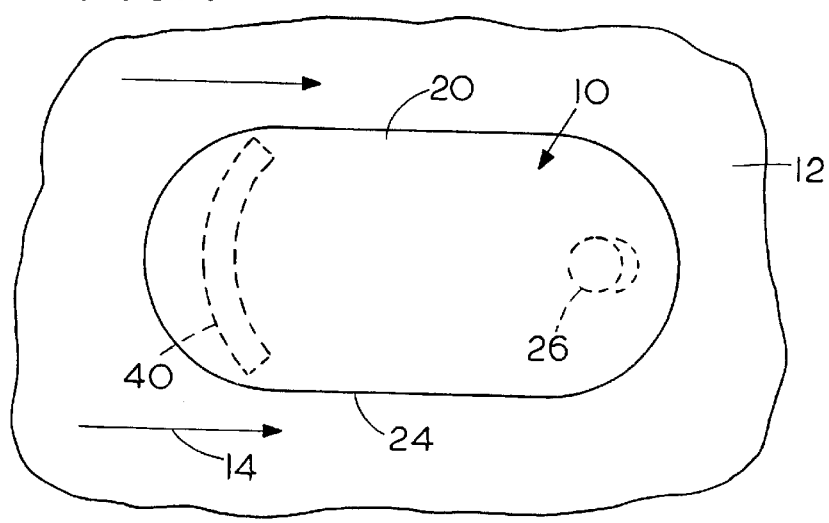
FIG. 1 is a plan view of a typical acoustic guided wave plate forming an ultrasonic path, and including a self test construction made according to the present invention.
Figure 2:
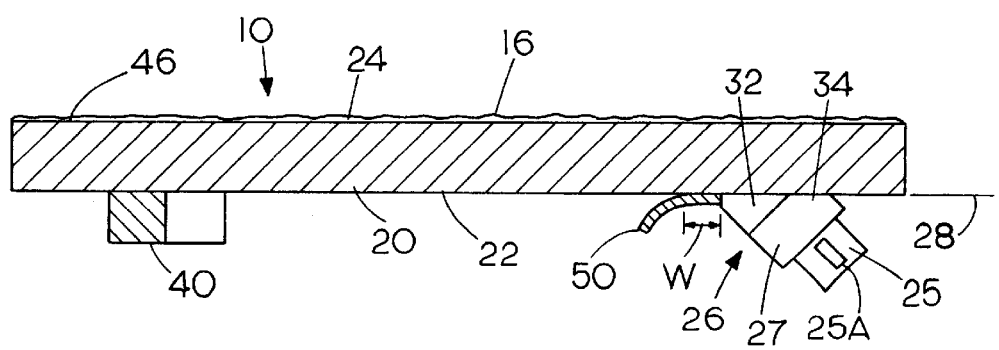
FIG. 2 is a sectional view of the sensor plate of FIG. 1.

Referring to FIG. 1, an acoustic (ultrasonic frequency range) contaminant sensor assembly 10 is shown schematically in position along the upper skin or wall 12 of an aircraft wing. As shown, the acoustic sensor assembly 10 extends essentially in a direction parallel to the airflow across the wing, which is shown by the arrows 14. The wing can be constructed in any desired manner, and the acoustic sensor assembly 10 is made to sense contaminants, such as ice illustrated in FIG. 2 at 16, on the exterior surface of the wall or plate that is ultrasonically vibrated. The acoustic sensor assembly 10 comprises a wall or plate 20 that has a length that is parallel to the direction of airflow, and as shown parallel to the chord of the wing or aircraft wall 12. The sensor wall or plate 20 is fastened in place with suitable fasteners such as flush rivets or by bonding the parts. The wall or plate 20 may be the structural wall, such as the skin or wall 12 of an aircraft. Various configurations of contaminant detection systems are shown and discussed. in Rose et al. U.S. Pat. Nos. 5,629,485 and 5,932,806. For illustrative purposes, the plate or wall 20 is shown as a uniform thickness plate. The wall or plate 20 has an interior surface 22, as well as an exterior surface 24 on which the ice shown at 16 accumulates.

Ultrasonic or acoustic energy that causes acoustic vibration in the wall or plate 20 is provided by a transducer assembly indicated generally at 26. The transducer assembly can be of any desired type, for example the type shown in U.S. Pat. No. 5,922,958, and is the transmitter preferably is a well known piezoelectric sensor element 25A. As illustrated, there is one transducer 25, mounted onto a housing 27. The housing 27 is supported with a wedge 32 so that the plane of the piezoelectric element 25A that sends acoustic energy and receives the reflected acoustic energy is at an angle relative to the general plane 28 of the wall or plate 20.

The transducer support wedge 32 is bonded with a bonding layer shown illustratively at 34 to the inner surface 22 of the wall or plate 20. The transducer 25 is at a first location on the wall or plate 20, as indicated, near one end of the sensor wall or plate.

When the transducer 25 is energized by suitable processor circuitry 30, the transmitter section 25A will provide a desired vibration pattern (in the form of a Lamb wave) on the outer surface 24 of the wall or plate 20. This is discussed in the. Rose et al. U.S. Pat. No. 5,629,485.

The processor circuit 30 is of known design and is connected to the transducer 25 for providing excitation for the transducer 25 to create an acoustic wave in the wall or plate 20 during a first time period, and for receiving and processing a return signal, typically a frequency vs. amplitude signal, during one or more second time periods, in a known manner. In other words, the transmitter section of transducer 25 transmits the ultrasonic signal forming an acoustic energy wave, and then the transmitter portion turns off.

The transducer 25 then has a section that acts as a receiver to receive a reflected wave at certain times or time windows. The transducer thus determines presence of a reflected or return ultrasonic vibration. A separate receiver also can be used for such detection of return signals. As shown, the plate 20 has a contaminate detecting first ultrasonic wave reflector, shown as a bonded on bar reflector 40 defined adjacent an opposite end of the plate, and extending transversely to the direction, indicated by the arrow 42, of transmission of the ultrasonic wave. The direction of reflected waves is indicated generally at 44. The reflector 40 forms a wave reflecting surface for the ultrasonic vibration signal to be echoed back to the transducer assembly 26 and sensed by the transducer 25. The reflector 40 can be formed to reduce bouncing of the ultrasonic wave in the reflector. The reflector can be replaced with a groove formed in either the top or bottom surface of wall or plate 20, if desired.

The transducer support wedge 32 is bonded securely to the inner surface 22, but it is known that this bonding can become loose or fail. Also, ultrasonic transmitters can fail. As stated, this disbanding is a serious problem with ultrasonic sensors, since poor bonds resulted in spurious signals and shortened sensor life. During the occurrence of heavy plate contamination such as a buildup of a thick layer of ice 16, the guided wave signature received from the reflector 40 near the end of the plate or wall 20 disappears, and this indicates that the plate is truly contaminated, or the sensor is dead, or a disbond occurred. With the present invention, the plate or wall is provided with a self test reflector, as shown a waveguide 50 which extends laterally across the plate or wall generally parallel to the reflector 40, but positioned closely adjacent to the transducer 25. Preferably the waveguide 50 is secured to the plate or wall within the first ultrasonic wave length determined by the frequency and ultrasonic velocity in the plate.

Figure 5:
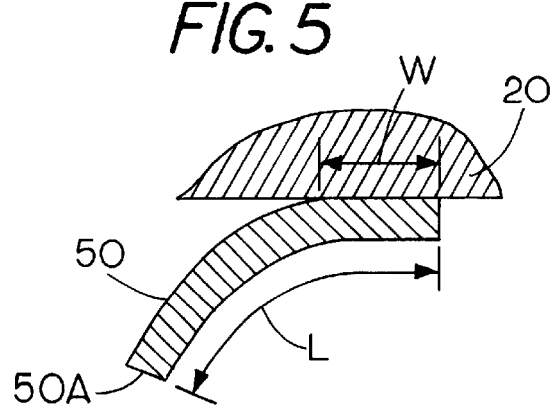
FIG. 5 is an enlarged fragmentary sectional view of a waveguide used as part of the self test construction shown in FIG. 2.

In FIG. 5, an enlarged view of the waveguide 50 is illustrated. The dimension of the reflector indicated by the double arrow W, is the length of the waveguide that is in contact with and bonded to the plate or wall 20, and the overall length of the travel path is indicated at L. This path follows the curve of the waveguide 50 as shown. The dimension W of the waveguide contacting the plate or wall should be greater than one wavelength of ultrasonic energy in the contaminate detection plate or wall 20. By satisfying this requirement, it is insured that the ultrasonic energy is transferred to the waveguide. The length L, which is the overall travel path of the waveguide is preferably designed such that the ultrasonic energy received back from the end of the waveguide indicated at 50A in FIG. 5, is of sufficient length so that the time between transmission of a signal and receipt of a reflected vibration signal by the transducer 25 will be sufficient to avoid mistaking disturbances or false signals from internal reflections for the self test signal. Such internal disturbances may occur in the transducer 25 or in the wedge or mounting block 32 between the transducer and the wall or plate 20.

Thus, selection or parameters for the waveguide insure that the correct reflected self test signal will be recognized.

Figure 6:
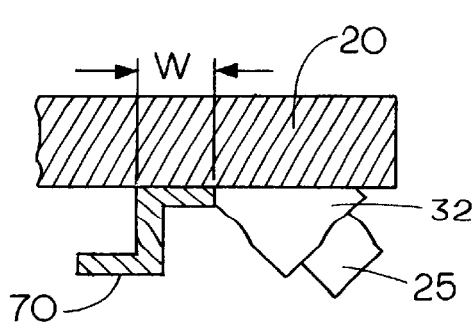
FIG. 6 is a side sectional view of a modified waveguide usable in the self test construction.

FIG. 6 shows an alternate form of the self test waveguide mounted relative to the transducer 25 and wedge 32, and in this case, the waveguide 70 is a wall that is formed to have offset sections. The length W again is the length that is in contact with and bonded to the plate or wall 20, and the overall travel length of the ultrasonic wave or vibration is the length following the offset sections to the outer end 70A of the waveguide 70.

Figure 7:
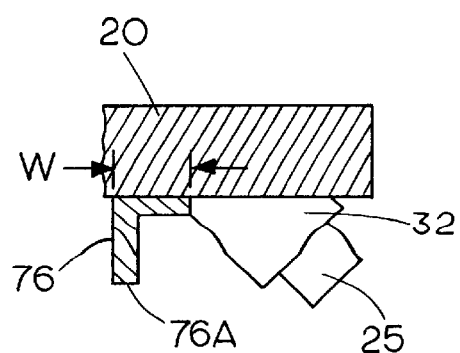
FIG. 7 is a further modified waveguide usable in the self test construction.

FIG. 7 is a further modified form of a self test waveguide that is in the shape of an angle iron. The length W is one leg that is in contact with and bonded to the plate or wall 20, and the overall length of the waveguide shown at 76 is from the end adjacent the wedge 32 at transducer 25, to the outer end 76A of the waveguide 76.

Other configurations of waveguides can also be used, within the parameters outlined.

Figure 3:
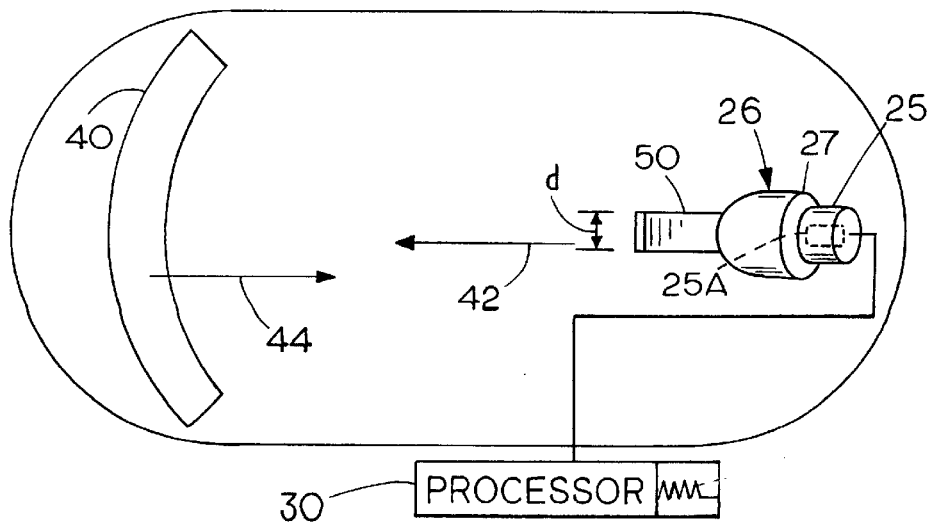
FIG. 3 is a bottom plan view of the plate of FIG. 1.

In FIG. 3, the waveguide 50 is illustrated in the preferred form as a curved member The dimension D, or the transverse width of the waveguide is kept to a minimum so that while insuring that the disturbance that it creates is enough to detect. In other words, the dimension D is selected to be minimized, but based upon the output of the transducer 25.

Instead of having the discontinuities or reflectors for reflecting ultrasonic vibrations, a separate receiver close to the transmitter at the position of waveguide 50, and another receiver adjacent the position of reflector 40 can be used to provide the self test procedure and the contaminate detection.

Figure 4:
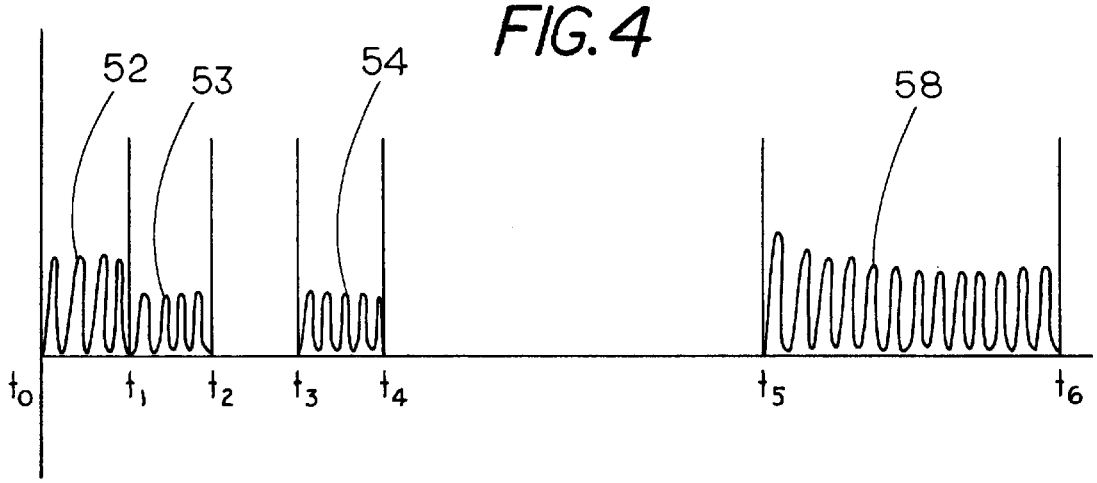
FIG. 4 is a schematic representation of a timing diagram illustrating the operation of the present invention.

The operation of the self test is illustrated in the timing diagram of FIG. 4. A transmitted signal shown in FIG. 4 at 52 is transmitted between times to and $t_1$, by the transmitter portion of transducer 25. Immediately after time $t_1$, up to time $t_2$ the receiver portion of transducer 25 is turned on, and if a signal 53 is received, it is known that the transmitter 25A is operable.

From time $t_2$ to time $t_3$, the receiver section of the transducer 25 is turned off.

At time $t_3$ the receiver section of the transducer again is turned or to "look for" a signal reflected from the self test reflector 50. A reflected signal indicated at 54 between times $t_3$ and $t_4$ is from the self test reflector, and if received it is known that the transducer is operable, and the bond needed to couple the ultrasonic energy or acoustic wave to the wall or plate 20 has not loosened or become non functional. It is then also known that the reflected signal from the main contaminant detection reflector 40, can be relied upon. The reflected signal from discontinuity is expected at a later time, as shown, between times $t_5$ and $t_6$, and indicated at 58 in FIG. 4, can be relied upon as representing a signature that indicates either no contaminants on the surface, or the presence of such contaminants.

The transducer 25 will provide an output electrical signal from the piezoelectric sensor element 25A that is part of the transducer 25. The techniques of transmitting and receiving ultrasonic vibrations are well known.

The time periods shown in FIG. 4 typically can be as follows: from $t_0$ to $t_1$, 150 µseconds; to $t_2$, 100 µseconds; to $t_3$, 150 µseconds; to $t_4$, 200 µseconds; to $t_5$, 350 µseconds and to $t_6$, 500 µseconds. The times for transmitting and for turning on the receiver depend on the overall length between the transmitter and main reflector, the wall material and power needed.

If a response is present between time $t_1$ and $t_2$, then transducer is functional, and if there is a response from the self test reflector between time $t_3$ and $t_4$, it is known that ultrasonic wave energy is coupled into the wall.

If responses are received between time $t_1$ and $t_2$ and between $t_3$ and $t_4$, then the receiver looks at responses between $t_5$ and $t_6$ to determine if ice is on the surface 24. No response would mean heavy ice and a large amplitude response would mean no ice. Amplitudes between the extremes would be a function of ice or other contaminant build up.

Again, typically, the first or self test reflector is designed to give a minimal reflection, and consecutive reflected signals from reflector 50 would be attenuated before time $t_5$, so the self test reflector will not affect the response from the main or detector reflector.

The processor is set up so that each time it energizes the transducer 25 to transmit a pulse, which is done at regular time intervals, the self test reflector, shown as waveguide 50 will reflect a signal that is substantially unaffected by contaminants because of its close proximity to the transducer assembly 26. The initial response between times $t_1$ and $t_2$ is a "ringing" of the transmitter rather than a reflected signal. The return signal from the self test reflector, which as shown, is not as severe a discontinuity as the main sensor reflector 40, will always indicate whether the transducer assembly is operable, or whether disbonding has occurred. The processor circuit is used for indicating when contaminants are present because of changes in the return signal received between times $t_5$ and $t_6$. The processor circuit 30 also is used for each transmission for the self test by setting the receiver portion to look for a return signal at the time (t3 to t4) when a return can be expected, based on the spacing of the waveguide 50 from the transducer 25 and the path length L of the waveguide.

While the reflectors 40 and 50 have been illustrated, it is to be understood that other types of reflectors can be utilized, such as grooves formed on the inner (or outer) surface 22 of the wall or plate 20, or, if the application of the sensor assembly is one that will permit it, reflectors on the exterior surface also can be used for providing a disruption of the transmitted acoustic signal that will provide a reflection adequate for the transducer 25 to sense it. It is common to have a bar on the interior surface, or some other discontinuity that will perform the same function as the reflectors. The reflectors thus encompass grooves, bars, and other irregularities, such as a rivet assembly, which can be used for the self test reflector. An interface between different materials at the location of the reflector, also can serve as a reflector.

It also should be noted that the reflector 50 can be curved as shown or in other words made to form an arc to provide a reflector that will to focus the reflected waves back toward the transducer 25. The wall or plate material also can be of any desired type, and while a piezoelectric element 25A is commonly used, other types of ultrasonic generators can be utilized as well. As stated, separate transmitters and receivers can be used, and bonded to the interior surface 22 of the plate. The wall acting as the ultrasonic or acoustic energy transmitting wall can be the actual structural wall.

Although the present invention has been described with reference to preferred embodiments, workers skilled in the art will recognize that changes may be made in form and detail without departing from the spirit and scope of the invention.

What is claimed is:

1. A sensor comprising a wall having a surface for transmitting ultrasonic vibrations, a transducer coupled to the wall for transmitting a pulse forming an ultrasonic acoustic wave that propagates along the surface of the wall, a receiver for receiving a first signal indicating that the ultrasonic wave has been transmitted along the surface of the wall a first distance, and a receiver for receiving a second signal indicating the ultrasonic wave has been transmitted a second distance substantially less than the first distance to provide an indication that the transducer is acoustically coupled to the wall, wherein the first distance and the second distance extend parallel to the wall.

2. The sensor of claim 1, further comprising an ultrasonic wave reflector at a location spaced the first distance from the transducer, the receiver receiving the first signal being part of the transducer.

3. The sensor of claim 1, wherein the second signal is an ultrasonic signal reflected from a second self test reflector and the receiver for the second signal is part of the transducer.

4. The sensor of claim 3, wherein said self test reflector is positioned relative to the transducer such that the reflected signal is substantially unaffected by contaminants on the wall.

5. The sensor of claim 3, further comprising a processor to determine the presence of the second reflected signal in a selected time period after transmitting a pulse, to indicate that the transducer is acoustically coupled to the wall.

6. The sensor of claim 5, wherein said transducer is bonded to a surface of the wall, and the second signal from the self test reflector changes if the bonding between the transducer and the wall changes.

7. The sensor of claim 1, wherein said transducer comprises a transducer assembly of a transmitter and a receiver, and the assembly is bonded to a surface of the wall.

8. The sensor of claim 7, wherein the receiver for receiving the first signal and the receiver for receiving the second signal are the same receiver forming part of the transducer assembly.

9. The sensor of claim 7, wherein said self test reflector comprises a waveguide bonded to the wall, said transducer assembly being bonded to the wall on the same surface as the waveguide.

10. The sensor of claim 9, wherein the waveguide is a guide having a first surface portion bonded to the wall and having a second portion spaced from the wall.

11. The sensor of claim 9, wherein the waveguide is a guide wall having a length, a first portion of the length being bonded to a surface of the sensor wall for transmitting ultrasonic vibrations into the waveguide and the guide wall having a second portion of the length spaced from the surface.

12. The sensor of claim 11, wherein the first portion of the length of the guide wall is greater than one wavelength of the ultrasonic acoustic wave.

13. The sensor of claim 12, wherein the second portion of the length of the guide wall is curved away from the surface.

14. The sensor of claim 12, wherein the guide wall has an offset section comprising the second portion of the length of the guide wall.

15. The sensor of claim 12, wherein the second portion of the length of the guide wall is perpendicular to the surface.

16. The sensor of claim 4, wherein said self test reflector is positioned a distance from the transducer that is no more than the wavelength of the transmitted ultrasonic wave.

17. The sensor of claim 2, wherein said reflector comprises a bar raised from the wall and the first distance spaces the reflector from the transducer a sufficient amount so that contaminants on a surface of the wall affect a reflected signal received by the transducer from the reflector.

18. The sensor of claim 1, wherein said transducer comprises a piezoelectric element.

19. A sensor for detecting contaminants on a wall having opposite surfaces, a first of the surfaces being exposed to ambient conditions and on which contaminants can collect, a second of said surfaces having a first ultrasonic reflector thereon, a transducer assembly mounted on the second surface at a location spaced from the first ultrasonic reflector a first distance, the transducer assembly being capable of transmitting ultrasonic energy through the wall toward the first ultrasonic reflector, and being capable of receiving reflected signals from the first ultrasonic reflector to provide an output indicating receiving the reflected signals, and a second self test reflector positioned on the wall adjacent the transducer assembly to provide a signal indicating reflected ultrasonic energy transmitted by the transducer assembly that is substantially unaffected by contaminants on the surface of the wall exposed to ambient conditions, wherein the second self test reflector comprises a waveguide having a width extending lateral to a direction line extending between the transducer assembly and the first ultrasonic reflector that is substantially less than the width of the first ultrasonic reflector.

20. The sensor of claim 19, wherein said transducer assembly forms a bond with the second surface of the wall, and the signal reflected from the second self test reflector changes when the condition of the bond between the transducer assembly and the second surface of the wall changes.

21. The sensor of claim 19, wherein the first ultrasonic reflector comprises a raised bar on the second surface of the wall.

22. A method of testing an ultrasonic contaminant sensor for operability, the contaminant sensor comprising a transducer coupled to a wall having a surface so as to transmit ultrasonic waves along the wall, wherein the ultrasonic waves propagate along and parallel to the surface of the wall, the method comprising providing a first ultrasonic wave reflector on the wall at a first distance from the transducer, providing a second test ultrasonic wave reflector on the wall a second distance from the transducer which is substantially shorter than the first distance, wherein the first distance and the second distance extend along the wall, transmitting an ultrasonic wave signal from the transducer and receiving ultrasonic wave signals at a time subsequent to transmitting to determine whether the ultrasonic waves are reflected from the second test reflector.

23. The method of claim 22 comprising placing the second test reflector at a distance from the transducer such that contaminants do not substantially affect the received ultrasonic wave signals reflected from the second test reflector.

24. The method of claim 23, including selecting the distance the second test reflector is placed from the transducer to be no more than one wave length of the transmitted ultrasonic signal.

25. The method of claim 23, comprising selecting the first distance so that reflections from the first reflector are attenuated when reflected signals from the first reflector are received by the transducer.

26. The method of claim 22, comprising transmitting ultrasonic energy for a first time period and at an end of the first time period receiving vibration signals from the wall for a second time period to determine if ultrasonic energy has been transmitted to the wall.

27. A method for testing an ultrasonic contaminant sensor for operability, the method comprising:

providing a wall having opposite surfaces, a first of the surfaces being exposed to ambient conditions and on which contaminants can collect;

providing a transducer assembly mounted on the second surface at a location spaced from the first ultrasonic reflector a first distance;

providing a first ultrasonic reflector having a width mounted on a second of said surfaces and a second self test reflector positioned on the wall adjacent the transducer assembly, wherein the second self test reflector comprises a waveguide having a width, the width of the first ultrasonic reflector and the width of the wave guide lateral to a direction line extending between the transducer assembly and the first ultrasonic reflector, wherein the width of the waveguide is substantially less than the width of the first ultrasonic reflector;

transmitting an ultrasonic wave signal from the transducer assembly; and, receiving ultrasonic wave signals at a time subsequent to transmitting to determine whether the ultrasonic waves are reflected from the second self test reflector.

* * * * *

UNITED STATES PATENT AND TRADEMARK OFFICE
CERTIFICATE OF CORRECTION

PATENT NO.    : 6,568,270 B2
DATED         : May 27, 2003
INVENTOR(S)   : Derrick D. Hongerholt It is certified that error appears in the above-identified patent and that said Letters Patent is hereby corrected as shown below:

<u>Column 6,</u>
Line 43, cancel "along" and insert -- parallel to -- after "of" insert -- and along --;
Line 45, cancel "the surface of";
Line 51, cancel "parallel to" and insert -- along the surface of --.

Signed and Sealed this

Ninth Day of November, 2004

JON W. DUDAS
*Director of the United States Patent and Trademark Office*

UNITED STATES PATENT AND TRADEMARK OFFICE
CERTIFICATE OF CORRECTION

PATENT NO. : 6,568,270 B2
DATED : May 27, 2003
INVENTOR(S) : Derrick D. Hongerholt It is certified that error appears in the above-identified patent and that said Letters Patent is hereby corrected as shown below:

Column 6,
Line 43, cancel "along" and insert -- parallel to --; after "of" insert -- and along --;
Line 45, cancel "the surface of";
Line 51, cancel "parallel to" and insert -- along the surface of --.

Signed and Sealed this

Seventh Day of December, 2004

JON W. DUDAS
*Director of the United States Patent and Trademark Office*